United States Patent
Lenz et al.

[11] Patent Number: 6,026,315
[45] Date of Patent: Feb. 15, 2000

[54] METHOD AND APPARATUS FOR CALIBRATING A NAVIGATION SYSTEM IN RELATION TO IMAGE DATA OF A MAGNETIC RESONANCE APPARATUS

[75] Inventors: Gerald Lenz, Neunkirchen am Brand; Rainer Kuth, Herzogenaurach; Theodor Vetter, Erlangen, all of Germany

[73] Assignee: Siemens Aktiengesellschaft, Munich, Germany

[21] Appl. No.: 09/044,248

[22] Filed: Mar. 19, 1998

[30] Foreign Application Priority Data

Mar. 27, 1997 [DE] Germany .......................... 197 13 122
Feb. 9, 1998 [DE] Germany .......................... 198 05 112

[51] Int. Cl.⁷ .................................................. A61B 5/055
[52] U.S. Cl. .......................... 600/414; 600/411; 600/417; 606/130
[58] Field of Search .................................. 600/410, 414, 600/417, 411, 426, 427, 429; 324/318, 322; 606/130

[56] References Cited

U.S. PATENT DOCUMENTS

| | | |
|---|---|---|
| 4,923,459 | 5/1990 | Nambu . |
| 5,622,170 | 4/1997 | Schulz ...................................... 600/429 |
| 5,662,111 | 9/1997 | Cosman .................................... 600/417 |
| 5,678,549 | 10/1997 | Heywang-Koebrunner et al. . |
| 5,682,890 | 11/1997 | Kormos et al. .......................... 600/417 |
| 5,891,034 | 4/1999 | Bucholz .................................. 600/427 |

*Primary Examiner*—Ruth S. Smith
*Attorney, Agent, or Firm*—Hill & Simpson

[57] ABSTRACT

In a method and apparatus for calibrating a navigation system in relation to image data of a magnetic resonance apparatus, positions of at least three markers arranged in an imaging volume of a magnetic resonance apparatus are determined with the navigation system in a first coordinate system, and are determined by means of magnetic resonance in a second coordinate system. From the positions of the markers in the two coordinate systems, a position and an orientation of the two coordinate systems to one another are determined. Localization data are transformed into the second coordinate system. An apparatus for conducting the method has at least one marker having a substance that can be detected using magnetic resonance technology, in spatial allocation to optical markings. A pickup coil can be spatially allocated to each marker.

3 Claims, 6 Drawing Sheets

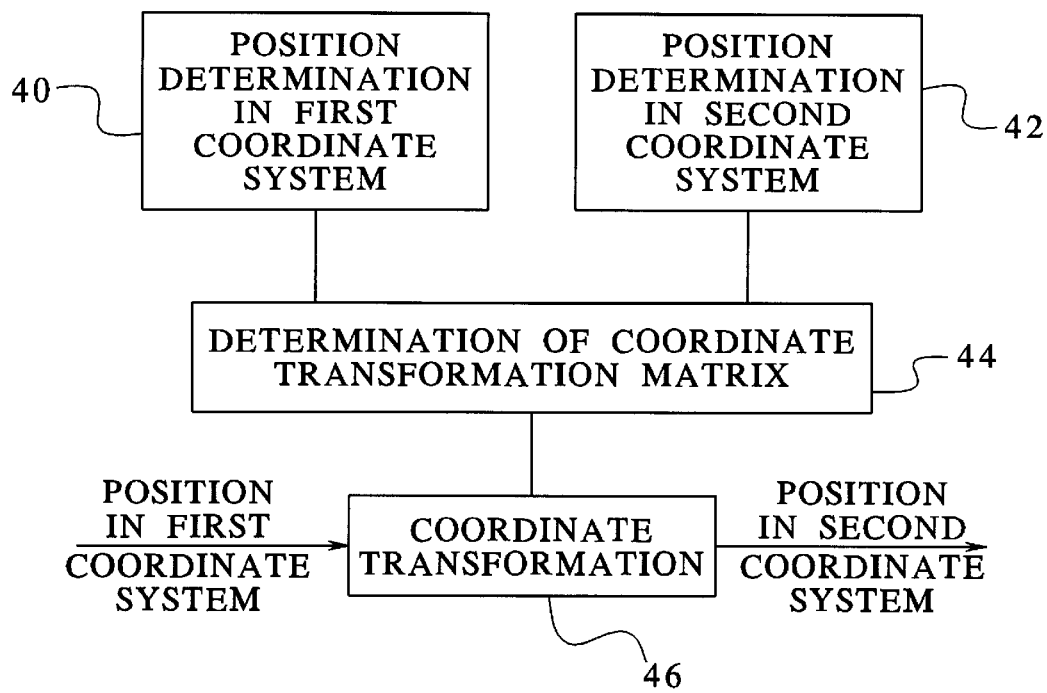
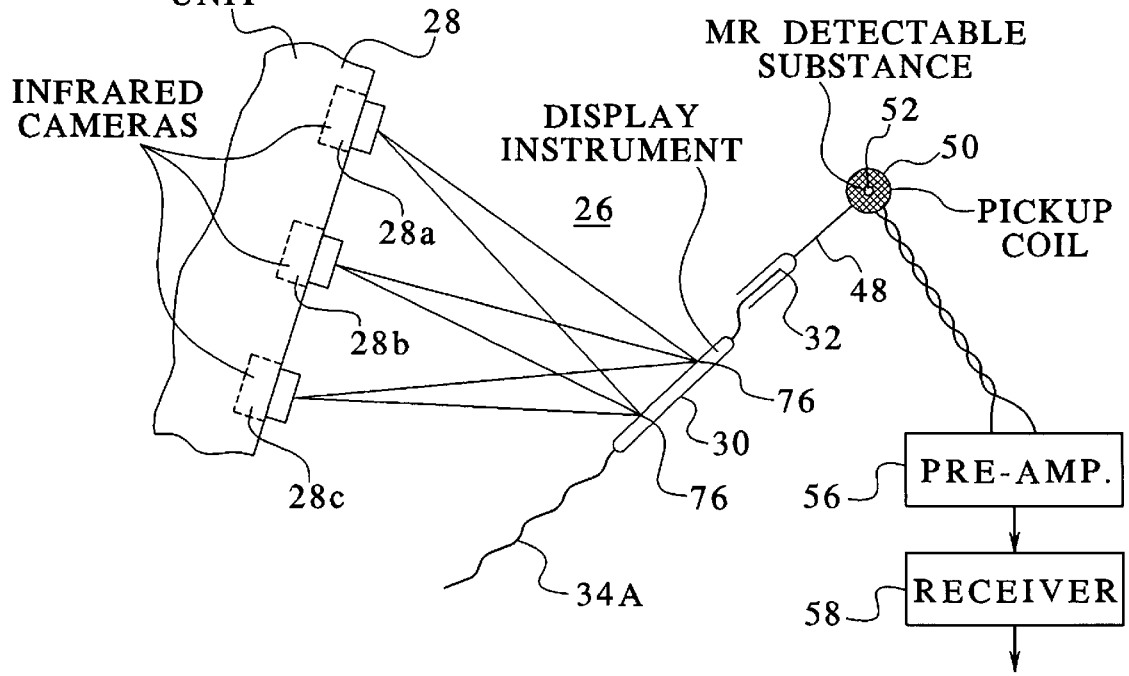

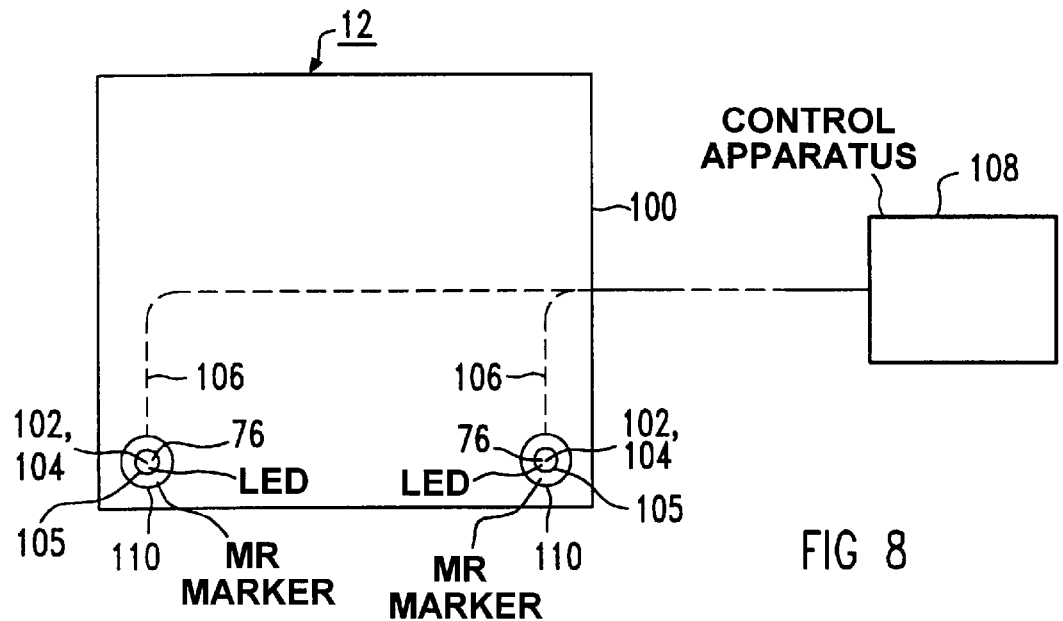
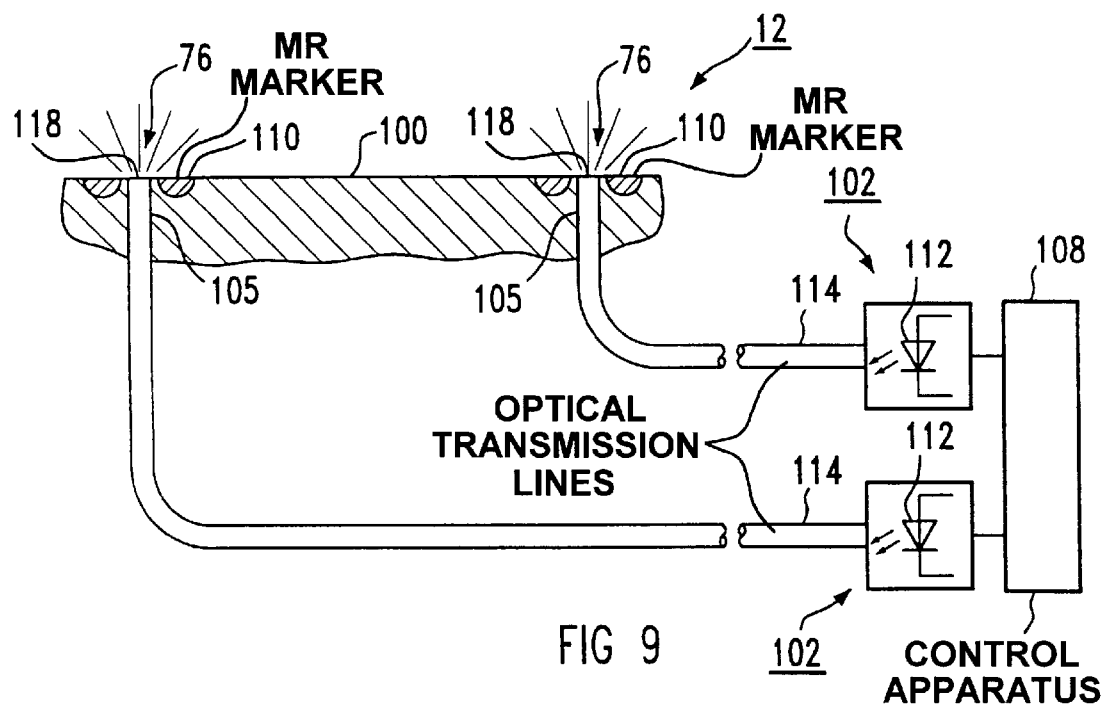

METHOD AND APPARATUS FOR CALIBRATING A NAVIGATION SYSTEM IN RELATION TO IMAGE DATA OF A MAGNETIC RESONANCE APPARATUS

BACKGROUND OF THE INVENTION

1. Field of the Invention

The present invention relates to a method for calibrating a navigation system, of the type which generates localization data in a first coordinate system, in relation to image data, the image data being produced by a magnetic resonance apparatus in a second coordinate system. In addition, the invention relates to apparatuses for conducting the method.

2. Description of the Prior Art

The position of the coordinate system in a diagnostic magnetic resonance apparatus is determined by the basic field magnets, including shim elements and the gradient coil system. It can be indicated with a precision up to a few millimeters in relation to the outer covering of the apparatus. A patient is, for example, placed in the imaging volume using a laser light sight attached to the covering of the magnetic resonance apparatus, the sight having a known distance to a midpoint—defined by the housing, of the imaging volume. For many magnetic resonance measurements, the precision thus achieved is sufficient. In certain cases, e.g. if the representation of symmetries in the body in the magnetic resonance image data set is concerned, a scan known as a scout scan is carried out before the actual determination of the image data, wherein sectional images in axial, coronal and sagittal orientations produced precisely through the center of the magnetic resonance coordinate system. On the basis of these three sectional images, the position of the patient in the magnetic resonance apparatus is corrected.

Primarily in neurosurgery, navigation systems are increasingly used in order to increase surgical precision, and in order to improve degree of radicality in an operation on tumors. In general, in neuronavigation particular position points in the operating field are projected on preoperative sectional image data. In this way, the surgeon can determine the position of deeper-lying structures or lesions in the operating field by means of the sectional image data, and thus can minimize the access path.

In neuronavigation, the image data coordinate system must first be brought to coincide with the patient coordinate system using the navigation system, i.e., the navigation system must be calibrated. Conventionally, for this purpose markers, visible in the sectional image, are attached to various points on the surface of the head before image data are recorded. After the patient has then been fixed for the operation, the markers imaged in the image data set can be marked with a mouse or with cross hairs. The markers are likewise located using a display instrument (pointer) of the navigation system. In this way, an image data computer can allocate the various marker points, and can bring the coordinate systems into coincidence. This method not only is time-consuming, but also conceals various sources of error. For example, the markers on the skin may move after being affixed to the head. Imprecisions also result if the marker points are not marked precisely with the cross-hairs. Another source of error can occur if the tip of the display instrument of the navigation system cannot meet the marker center precisely.

In order to allow displacements of the brain anatomy after the opening of the skull, or due to the use of brain spatulas, to be taken into account, in recent practice the 3D magnetic resonance sectional image data for the navigation system are newly acquired during the operation, using a magnetic resonance apparatus used intraoperatively; i.e., the basis for the navigation system is no longer a 3D image data set produced preoperatively, but rather a current image data set recorded intraoperatively after shifts or displacements of the brain anatomy.

For various interventions, such as freehand biopsies or brain biopsies without stereotactic frames, as well as for many interventional techniques with magnetic resonance sectional image guiding (MR guiding), it is useful to integrate the navigation system directly into the magnetic resonance apparatus. In this way, it is possible, for example, to set a particular position of the sectional image interactively at the patient, or, given coupling of the display instrument of the navigation system with the biopsy needle, to ensure that the image slice constantly follows the position of the biopsy needle. In this case, biopsies can be carried out extremely rapidly and with high precision. Similar to the way described above, it is necessary to make the coordinate system of the magnetic resonance apparatus (which in this case is identical to the patient coordinate system) known to the navigation system; i.e., the navigation system must be calibrated.

Conventionally, for the calibration of the navigation system, points on a surface of the magnetic resonance apparatus have been approached with the tip of the display instrument of the navigation system, the position of these points relative to the magnetic midpoint (which is at the same time the center of the patient coordinate system or of the image data coordinate system) being known. Since the distance of the housing points to the magnetic midpoint always has a tolerance that cannot be disregarded, and in addition the magnetic midpoint also depends on the adjustment of the gradient system, this type of calibration is subject to considerable error.

From German OS 43 25 206 and German PS 38 31 278, orientation arrangements are known that permit measurement of distances, e.g. of anatomical details, in a slice of a subject under examination in a corresponding tomogram, using markers.

SUMMARY OF THE INVENTION

An object of the present invention is to provide a method and apparatus with which a navigation system can be calibrated to the image data system more precisely in comparison to known methods.

This object is achieved in a first embodiment of the inventive method, wherein respective positions of at least three markers arranged in an imaging volume are determined with the navigation system in the first coordinate system, and are determined by means of magnetic resonance in the second coordinate system; from the respective positions of the markers in the two coordinate systems, a position and an orientation of the two coordinate systems relative to one another are determined; and localization data determined in the first coordinate system are transformed into the second coordinate system by means of the known relative position and orientation of the two coordinate systems to one another.

In a second embodiment, at least three different positions of a single marker in an imaging volume are determined with the navigation system in the first coordinate system and by means of magnetic resonance in the second coordinate system; from the positions of the marker in the two coordinate systems, a position and an orientation of the two coordinate systems relative to one another is determined;

and localization data determined in the first coordinate system are transformed into the second coordinate system by means of the known relative position and orientation of the two coordinate systems to one another.

The two alternative calibration embodiment have in common that the position(s) of the navigation marker(s) is (are) measured directly with the magnetic resonance apparatus, with which the patient image data are then also recorded.

The position of the markers in the second coordinate system may be acquired with at least one pickup coil. The determination of the position of the markers is thereby simplified considerably. The sensitivity of the pickup coil is limited to its immediate surroundings, and it is ensured that only signals of the imaging substance of the allocated marker are evaluated.

In a further version a pickup coil is allocated to each marker, and each pickup coil receives magnetic resonance signals that are emitted by the corresponding marker.

In another version for the determination of the positions of the markers in the second coordinate system, for each coordinate direction a non-selective magnetic resonance excitation pulse acts on the marker(s), and magnetic resonance signals thereupon emitted by the marker(s) are locus-coded during reception with the pickup coils with a gradient field, in the direction of the corresponding coordinate direction. If suitable methods for refocusing the magnetic resonance signals are used, the position of a marker in all three coordinate directions can be determined after a single excitation pulse.

If only one evaluation channel is available in the magnetic resonance apparatus, according to a further embodiment the pickup coils can be connected in chronologically successive fashion with the evaluation channel of the magnetic resonance apparatus.

The time required for calibration can be shortened considerably in a further version, wherein the magnetic resonance signals of several pickup coils are received simultaneously, the pickup coils being respectively connected to an evaluation channel of the magnetic resonance apparatus. Several evaluation channels fashioned for the connection of antenna arrays are provided in magnetic resonance apparatuses.

In a further version, errors in the determination of the position due to noise can be reduced if the positions are determined several times in the second coordinate system and then subjected to an average value formation.

In the apparatus for calibration, a marker including a substance that can be detected by magnetic resonance technology is arranged in the center of a pickup coil, and the pickup coil with the marker is fastened to a holder, and the holder has an opening for acceptance at least of a part of a display instrument of the navigation system. Since the center of the marker with the pickup coil for the display instrument of the navigation system is not accessible, the holder defines distance of a probe tip of the display instrument to the center of the marker (and of the pickup coil) so that this distance is predetermined. Besides the location of the display instrument or of the probe tip, the navigation system also determines the direction; in this way, given a known distance, the midpoint of the marker can be determined with great precision using the navigation system.

In a further version a guide for the part of the display instrument is connected to the opening in the holder, this guide orienting the part toward the marker.

The time required for calibration can be shortened if, in a further version of the invention, at least three markers with allocated pickup coils are attached to the holder.

In another embodiment of the inventive apparatus for calibration, at least three optical markings and markers allocated to the markings are arranged on a holding part, the markers including a substance that can be detected using magnetic resonance technology. The position of the markers in the coordinate system of the magnetic resonance apparatus is determined e.g. by an evaluation of a 3D image data set.

In another version the optical markings are constructed as optical transmitters for substantially punctiform (point-like) emission of optical signals.

The operation of the calibration apparatus in the magnetic resonance installation requires that this apparatus be constructed from non-magnetic materials. Thus, the optical transmitters constitute non-magnetic light-emitting diodes that are mounted in the holding part.

In a further embodiment, the optical transmitters are light-emitting diodes that are arranged separately from the holding part, and optical transmission lines from the light-emitting diodes to the holding part, the ends of the optical transmission lines being fashioned in the holding part for the emission of the optical signals. The optical signals of the light-emitting diodes (which are typically slightly ferromagnetic) can then be coupled into optical transmission lines outside the patient chamber in the magnet, and fed to the holding part. The optical signals then exit from the holding part.

In a further embodiment, the markers are fashioned as a torus, with the optical marking being arranged in the midpoint of each torus. The midpoints of the toruses, which are easily identifiable in the magnetic resonance sectional image, coincide with the locations of the optical markings.

In another embodiment, the optical markings have a reflecting surface. Supply lines for controlling the optical markings are thereby not needed. An optical location and angle measurement system must then be used that can follow purely reflecting objects, such as for example the commercially available navigation system POLARIS Optical Tracking System of the company Northern Digital Inc., Waterloo, Ontario, Canada.

DESCRIPTION OF THE DRAWINGS

FIG. 2 shows an overview of the main method steps of the invention for calibrating the navigation system.

FIG. 3 shows a first embodiment of an inventive apparatus for calibrating the navigation system.

FIG. 8 shows a side view of a fourth embodiment of an inventive apparatus for calibration, with non-magnetic light-emitting diodes as optical markings.

FIG. 9 shows a sectional representation of optical transmitters with light-conducting fibers used in the inventive apparatus.

DESCRIPTION OF THE PREFERRED EMBODIMENTS

Figure 1:
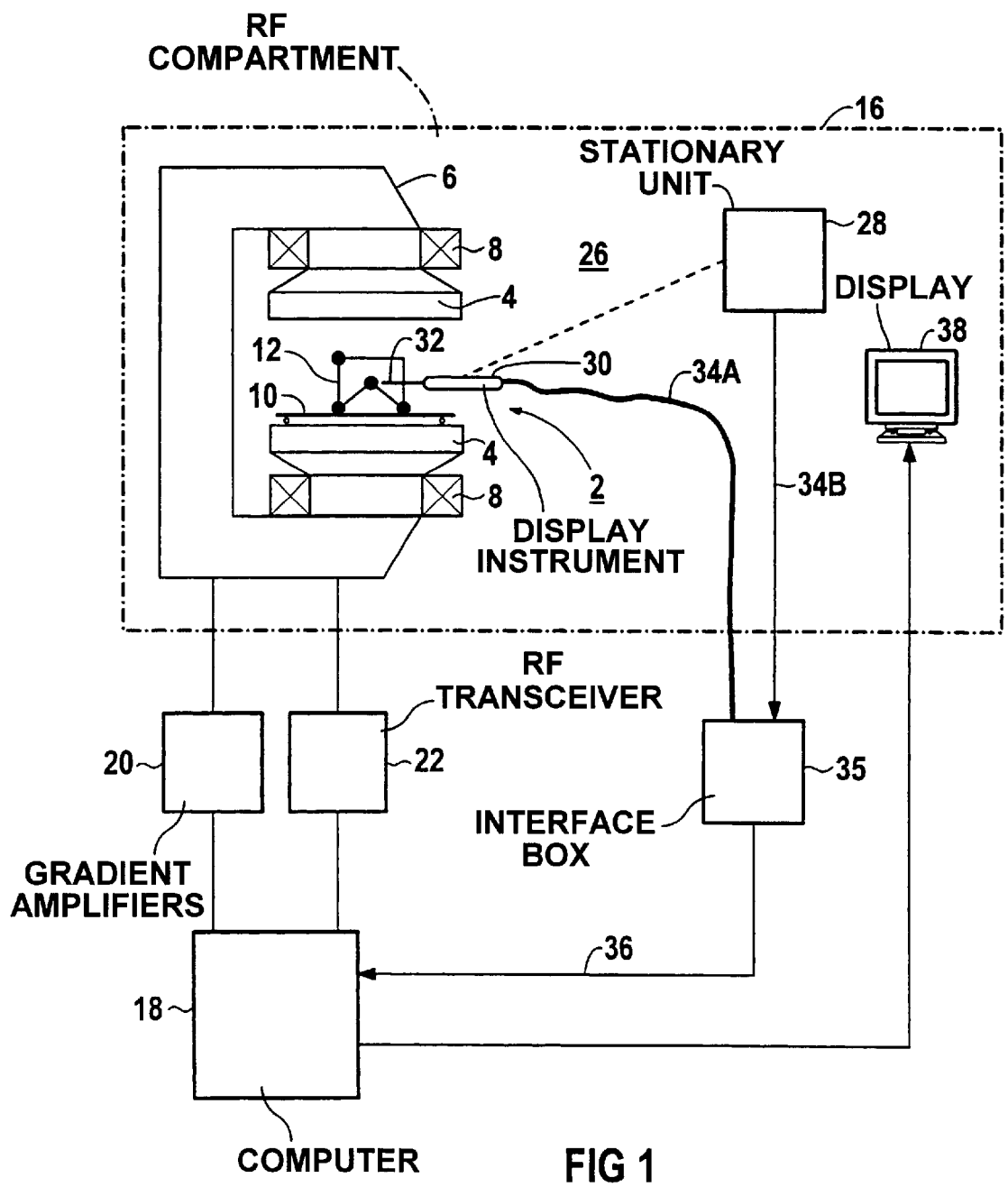
FIG. 1 shows a schematic representation of a diagnostic magnetic resonance apparatus with an navigation system that can be calibrated according to the invention.

The diagnostic magnetic resonance apparatus shown in an overview in FIG. 1 has an open magnet system 2 with two pole shoes 4 arranged opposite one another, which are connected with one another via a C-shaped magnetic return 6. A magnetic drive consists of a respective electromagnetic windings 8 arranged on the pole shoes 4. The magnetic system produces a basic magnetic field that is homogenous and vertically oriented, between the pole shoes 4 in a more or less spherical region. On a patient table 10, a phantom 12 is positioned within the homogenous basic magnetic field region by means of which a calibration of localization data to image data takes place. The function and construction of the phantom 12 are described in more detail below. In addition to access to the patient, the open magnet system 2 provides a physician or examining personnel with a lateral access that enables interventions to be carried out on a pacarried out on a patient. Not shown in FIG. 1 are the known gradient coils that are present in diagnostic magnetic resonance apparatuses for the production of gradient fields in three directions perpendicular to one another, as well as known RF antennas for the excitation or reception of the magnetic resonance signals. The magnet system 2, including the gradient coils and RF antennas, is located in an RF compartment 16. A control computer 18, which produces control signals required for operation and further processes magnetic resonance signals received from the RF antennas to form image data, is arranged outside the RF compartment 16. Also arranged outside the RF compartment 16 are gradient amplifiers 20 and an RF transceiver 22, whose operation is controlled by the control signals emitted by the computer 18.

Inside the RF compartment 16 there is a navigation system 26 that includes a stationary unit 28 and a display instrument 30. The stationary unit 28 includes a camera system that in general is not fixedly mounted, but can be individually repositioned according to the intervention. The camera system has multiple infrared cameras 28a, 28b and 28c. The display instrument 30 has a probe tip 32 whose position can be determined by the stationary unit 28 in the coordinate system of the navigation system. The display instrument 30 is connected with an interface box 35 arranged outside the RF compartment 16 via a first signal line 34A, and the stationary unit 28 is connected with this box via a second signal line 34B. For operation in the vicinity of the magnetic resonance apparatus, navigation systems suitable for use as the navigation system 26 are available that evaluate optical or acoustic signals for determining the position of the probe tip. A suitable navigation system that operates with optical signals is the POLARIS Optical Tracking System, of the company Northern Digital Inc., Waterloo, Ontario, Canada. The position data are communicated to the computer 18 via a third signal line 36.

An image representation unit 38 is arranged in the immediate vicinity of the magnetic resonance apparatus, in the field of view of the physician or examining personnel, on which the sectional images emitted intraoperatively by the computer, or also produced preoperatively, can be reproduced. In this way, the physician or examining personnel has the possibility of using the probe tip 32 to define a sectional plane on the patient of which an anatomical sectional image is to be produced intraoperatively, and a sectional image corresponding to the position of the probe tip 32 can also be selected from an image data set already produced preoperatively.

The above presupposes that the navigation system 26 is calibrated to the image data system, which is identical to the patient coordinate system. FIG. 2 shows the basic steps in the calibration. For this purpose, three positions in a first coordinate system are determined in the homogenous magnetic field region of the magnetic resonance apparatus, using the navigation system 26 (method step 40). The same three positions are determined in the second coordinate system using the magnetic resonance apparatus (method step 42). From the positions' associated coordinate values in the first and second coordinate systems, a coordinate transformation matrix is determined with relationships known from analytic geometry (method step 44). The coordinate transformation matrix indicates e.g. the position and direction of the first coordinate system in relation to the second coordinate system. In the current position acquisition with the navigation system, the positions acquired in the first coordinate system are transformed into coordinate values of the second coordinate system by means of this coordinate transformation matrix (method step 46).

FIG. 3 shows a first embodiment of the apparatus with which the navigation system 26 can be calibrated to the image data system. On the probe tip 32 of the display instrument 30, a pickup coil 50 with a spatially isotropic sensitivity distribution is attached, using a mount 48. The diameter of the pickup coil should be 1 to 2 mm in order to enable a point-precise measurement. In the center of the pickup coil 50, a substance 52 that can be detected by magnetic resonance technology is arranged as a marker, e.g. in the form of a small capsule filled with gadolinium or oil. Alternatively, a silicon mixture that can be detected by magnetic resonance technology can be used. It is also possible to use a liquid-filled ring arranged about the pickup coil 50 instead of a capsule.

The pickup coil 50 is connected via a preamplifier 56 with a receiver 58 belonging to the RF system of the magnetic resonance apparatus. Corresponding to the method specified on the basis of FIG. 2, the holder 48 is successively positioned at at least three different locations inside the imaging volume. These positions, which must not all lie in one plane, are acquired both with the navigation system 26 and with the magnetic resonance apparatus. The transformation matrix is then formed from the position values.

The determination of the position of the marker 52 by means of the magnetic resonance apparatus is explained below on the basis of FIGS. 4A to 4C and 5A to 5C.

Figure 4:
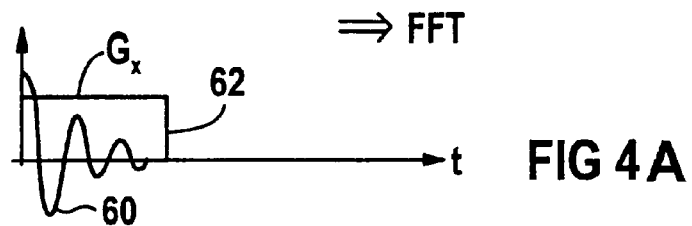
FIGS. 4A–4C show, in a time diagram, the signal curve of a locus coding of the magnetic resonance signals emitted by a marker.
Figure 4:
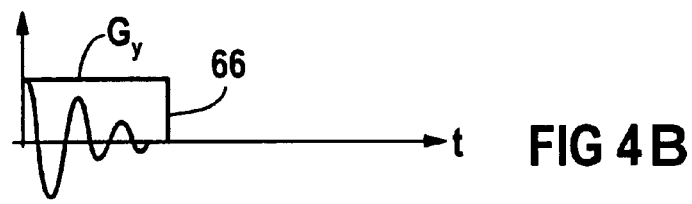
Figure 4:
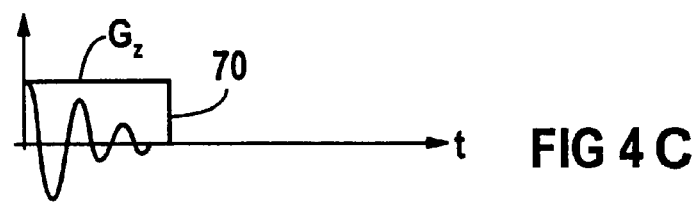
Figure 5:
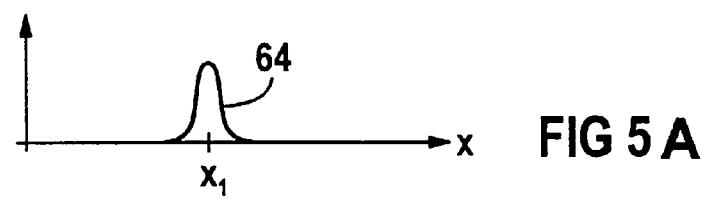
FIGS. 5A–5C show, in a diagram, signal curves of position signals after a decoding by Fourier transformation.
Figure 5:
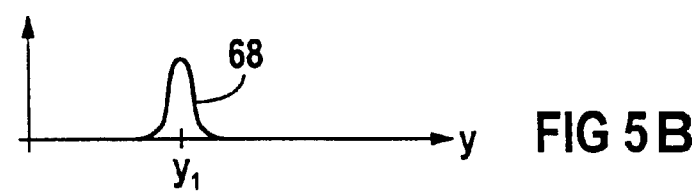
Figure 5:
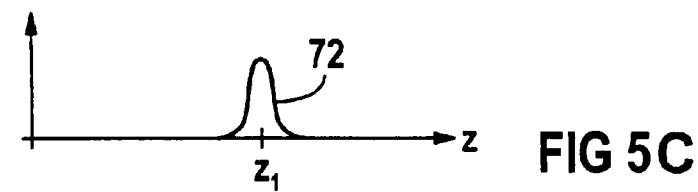

FIGS. 4A to 4C show, in section, three FID signals, which are received by the pickup coil 50 in succession after a non-selective excitation with an α RF pulse. FIG. 5A shows a locus coding in the x-direction of the magnetic resonance signal 60 emitted by the excited marker 52, by means of simultaneous production of a gradient field 62 the x direction. The frequency of the magnetic resonance signal 60 will arise depending on the position of the marker 52 in the gradient field. A Fourier transformation FFT of the received magnetic resonance signal 60 yields a signal peak 64, shown in FIG. 5A, at a frequency that corresponds to the coordinate value $x_1$ in the x-coordinate direction. Analogously, the position of the marker 52 in the y-coordinate direction is determined by the application of a gradient field 66 in the y direction, as shown in FIG. 4B. The Fourier transformation FFT supplies a signal peak 68 at the location $y_1$, shown in FIG. 5B. Likewise, the position of the marker 52 in the z-direction is thus obtained by the production of a gradient field 70 in the z-direction, as shown in FIG. 4C. The Fourier transformation supplies a signal peak 72 shown in FIG. 5C, with a frequency corresponding to the coordinate value $z_1$.

The signal peaks 64, 68 and 72 will be sharper as the dimensions of the marker 52 and of the pickup coil 50 are made smaller, however, with increasing miniaturization of the dimensions, the amplitude of the signal peaks 64, 68 and 72 also decreases. The probability of error in the determination of the position thus increases due to the worsened signal-to-noise ratio. Multiple measurements, with subsequent average value formation, can largely eliminate the errors caused by noise.

Figure 6:
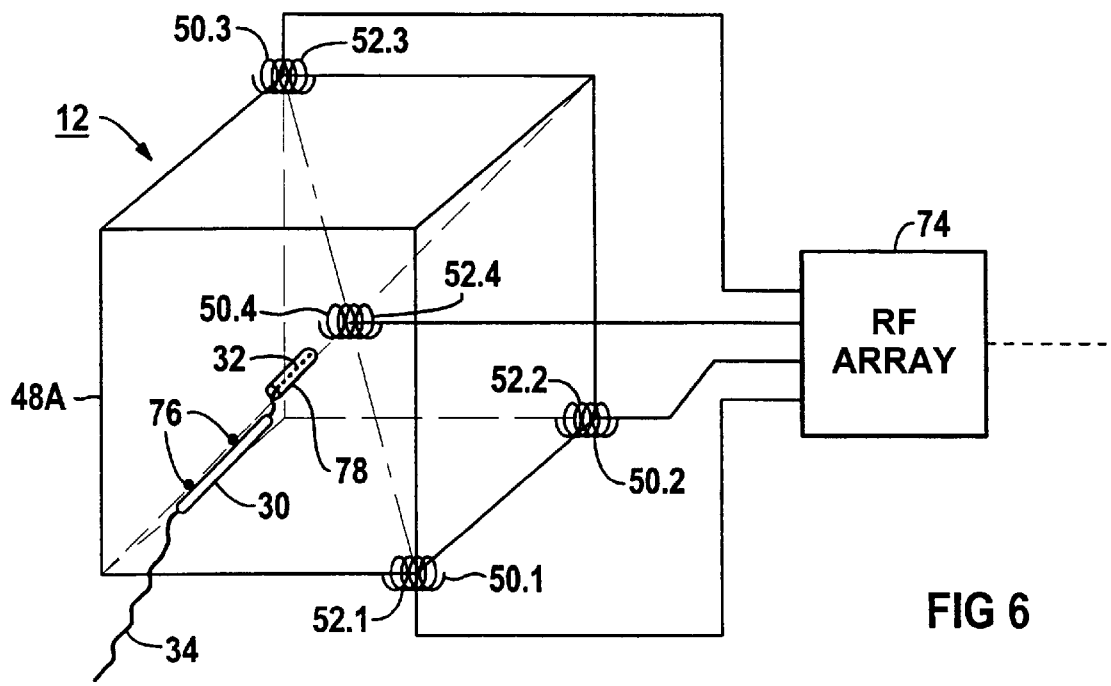
FIG. 6 shows a second embodiment of an inventive apparatus for calibrating the navigation system.

FIG. 6 shows a second embodiment of the apparatus, with which the navigation system can be calibrated to the image data system. Four pickup coils 50.1 to 50.4 are fastened on a holder 48A. In the center of the pickup coils 50.1 to 50.4 there are likewise located markers 52.1 to 52.4, which contain a substance that can be detected by magnetic resonance technology. The holder 48A is fashioned as a cubical frame with an edge length of about 10 cm, to which three pickup coils 50.1 to 50.3 with the appertaining markers 52.1 to 52.3 are fastened at the corners, and to which the pickup coil 50.4 with the marker 52.4 is fastened in the center. In the immediate vicinity of the pickup coils 50.1 to 50.4, there are arranged recesses that can accept the probe tip 32 at a defined spacing and with a predetermined direction. The pickup coils 50.1 to 50.4 are connected to an RF array 74, which has either a changeover switch, for the sequential connection of the pickup coils 50.1 to 50.4 with the receiver, or a four-channel receiver for the parallel processing of the received magnetic resonance signals. This embodiment simplifies handling in comparison with the embodiment shown in FIG. 3. As shown already in FIG. 1, this embodiment can be placed, for example, on the patient table 10 as a phantom 12. All the positions of the markers 52.1 to 52.4 can then be determined with the magnetic resonance apparatus, without further activity.

If the display instrument 30 of the optical navigation system 26 is equipped with more than three optical reference points 76 that are not arranged in a line, the navigation system can determine not only the direction of the display instrument 26 but also its rotational position. The position and orientation of the display instrument 30 can then be determined unambiguously.

In this case, the display instrument 30 is plugged at an endpoint into a tube-shaped opening 78 arranged in the holder 48A. The position and orientation of the tube-shaped opening 78 relative to the position of the pickup coils 50.1 to 50.4 with the markers 52.1 to 52.4 is known. For this reason, the positions—determined with the magnetic resonance apparatus—of the pickup coils 50.1 to 50.4 can be determined with the position of the display instrument 30 without further activity.

Figure 7:
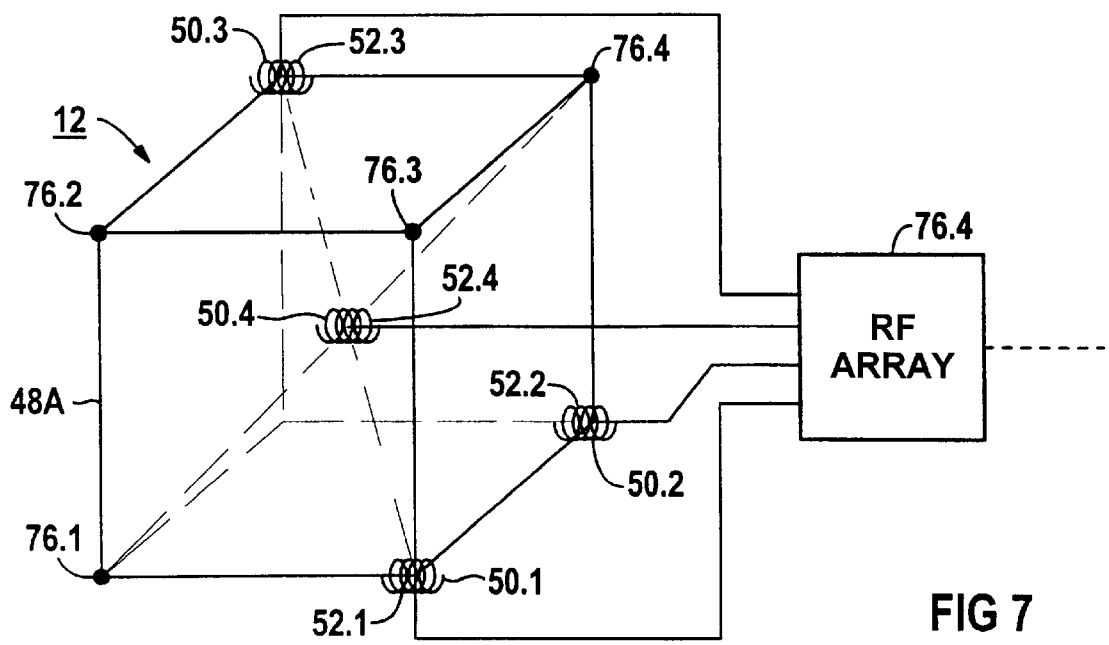
FIG. 7 shows a third embodiment of an inventive apparatus for calibrating the navigation system.

FIG. 7 shows a further embodiment of the phantom 12, in which four optical reference points 76.1 to 76.4 are attached to the cubical holder 48A at fixed and known distances to the pickup coils 50.1 to 50.4, which points can be recognized by the camera system arranged in the stationary part 28. Whereas the magnetic resonance apparatus can determine the position and orientation of the holder 48A in the coordinate system of the magnetic resonance apparatus via the position of the four pickup coils 50.1 to 50.4, the navigation system 26 can determine the position and orientation of the holder 48A in the coordinate system via the position of the four optical reference points 76.1 to 76.4. In this way, the calibration can be carried out without further activity.

FIG. 8 shows a side view of a further embodiment of a calibration arrangement with which the optical three-dimensional location and measurement system can be calibrated to the coordinate system of the diagnostic magnetic resonance apparatus. The calibration arrangement has a cubical holding part 100, wherein optical transmitters 102 for approximately punctiform emission of optical signals are installed in the vicinity of the corners as optical markings 76, which signals can be recognized by the optical location and angle measurement system (not shown). "Approximately punctiform" means that the spatial extension of the radiation surface of the optical transmitters 102 does not adversely affect the locus and angular resolution of the optical measuring system. As optical transmitters 102, non-magnetic light-emitting diodes 104 are used, which are distinguished primarily in that they are bonded to a ceramic substrate. The light-emitting diodes 104 are set into bored holes 105 in such a way that they can radiate light signals outwardly. On the side shown, two optical transmitters 102 are arranged, and on a further side there is at least one additional transmitter 102.

The light-emitting diodes 104 are connected with a control apparatus 108 via electrical connection lines 106. If the light-emitting diodes 104 are to be driven individually, e.g. cyclically, the electrical lines 106 are led individually to the control apparatus 108. Given a simultaneous driving of the light-emitting diodes 104, a single connection line to the control apparatus 108 is sufficient.

An annular marker 110, having a substance that can be detected by magnetic resonance technology, is arranged around each light-emitting diode 104. The markers 110 are, for example, filled with salt water.

FIG. 9 shows, in section, a further construction of the calibration means, which differs from the calibration means shown in FIG. 8 by a different construction of the optical transmitters 102. The optical transmitters 102 are normal light-emitting diodes 112, here arranged separately from the holding part 100, which are respectively coupled with an optical transmission line 114. The optical transmission lines 114 end in the holding part 100 in the bores 105. End surfaces 118 of the transmission lines 114 then radiate the optical signals.

For the calibration, the calibration arrangement is positioned approximately in the center in the imaging volume of the magnetic resonance apparatus, for example on a patient table. Using the magnetic resonance apparatus, the markers 110 are acquired, and the light points produced by the optical transmitters are acquired with the optical measuring system. A navigation software program obtains the coordinates of the markers 110 from the magnetic resonance image, as well as the locus coordinates of the allocated antimagnetic light-emitting diodes 104, or of the light exit surface 118, which were determined with the location and angular measuring system. Transformation parameters are then calculated from the coordinate values in the two coordinate systems.

Figure 10:
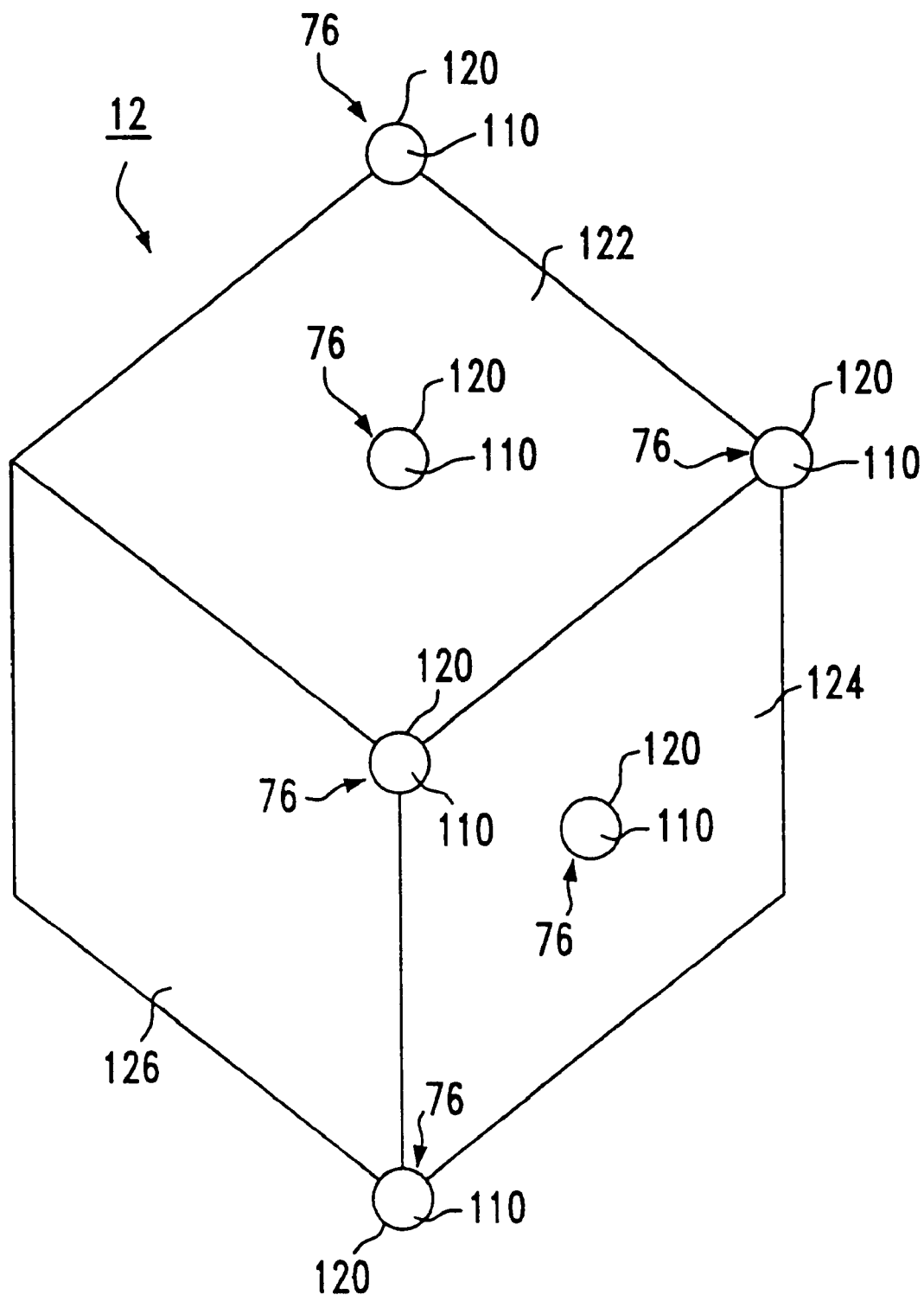
FIG. 10 shows a perspective view of a fifth embodiment of an inventive apparatus for calibration, with reflecting optical markings.

FIG. 10 shows a perspective view of a further embodiment of the calibration arrangement, wherein balls 120, e.g. with a surface that reflects infrared radiation, are used as optical markings. Overall, six balls 120 are fastened to two sides 122 and 124 of a cube 126. The cube 126 is constructed as a sealed hollow body, and is filled with a substance that can be detected by magnetic resonance technology. The location and the position of the cube 126 can be determined unambiguously from the shape and size of the sectional surface imaged in the magnetic resonance tomogram. The coordinate transformation can then be derived from the known arrangement of the optical markings 120 on the cube 126.

Alternatively, the balls 120 can be filled with a substance that can be detected by magnetic resonance technology, and from the size of the sectional surfaces visible in the magnetic resonance tomogram the coordinate transformation required for the calibration can likewise be determined. For the acquisition of the position with the navigation system, besides two infrared cameras an infrared radiation source is also required for the irradiation of the passive optical markers 120.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for calibrating a navigation system in a magnetic resonance apparatus having an imaging volume, comprising:

a phantom comprising a holder movable within said imaging volume and at least three optical markers mounted on said holder;

each of said optical markers having an infrared-reflecting exterior surface;

a navigation system having means for radiating said markers with infrared radiation;

two infrared cameras in said navigation system for obtaining optical image data of said markers irradiated with infrared radiation;

means in said navigation system for determining the respective positions of said markers in a first coordinate system from said optical image data;

said phantom containing a substance detectable in a magnetic resonance image;

means for obtaining a magnetic resonance image of said phantom, said magnetic resonance image containing magnetic resonance image data;

means for determining respective positions of said markers in a second coordinate system from said magnetic resonance image data;

means for determining, from the respective positions of said markers in said first coordinate system and in said second coordinate system, a relative position and a relative orientation of said first and second coordinate systems; and means for obtaining localization data in said first coordinate system using said navigation system and for transforming said localization data into said second coordinate system by employing said relative position and said relative orientation.

2. An apparatus as claimed in claim 1 wherein said holder comprises a hollow, sealed cube with said markers respectively mounted at different corners of said cube, said cube containing said substance detectable in a magnetic resonance image.

3. An apparatus as claimed in claim 1 wherein said markers comprise hollow sealed elements and wherein each of said markers contains said substance detectable in a magnetic resonance image.

* * * * *